United States Patent [19]
Fitz

[11] Patent Number: 6,129,700
[45] Date of Patent: Oct. 10, 2000

[54] CONTRAST MEDIUM INJECTION DEVICE AND METHOD OF USE

[75] Inventor: Matthew J. Fitz, Sunnyvale, Calif.

[73] Assignee: Advanced Cardiovascular Systems, Inc., Santa Clara, Calif.

[21] Appl. No.: 09/205,930

[22] Filed: Dec. 4, 1998

[51] Int. Cl.[7] .......................... A61M 1/00; A61M 29/00
[52] U.S. Cl. ....................... 604/30; 604/96; 606/191; 606/198
[58] Field of Search ................ 604/96, 102, 103, 604/264, 194, 915, 523, 536, 30, 35; 606/191–194, 198

[56] References Cited

U.S. PATENT DOCUMENTS

| | | |
|---|---|---|
| 4,564,014 | 1/1986 | Fogarty et al. .................... 128/344 |
| 4,641,654 | 2/1987 | Samson et al. . |
| 4,927,418 | 5/1990 | Dake et al. . |
| 4,968,306 | 11/1990 | Huss et al. . |
| 4,968,307 | 11/1990 | Dake et al. . |
| 5,012,044 | 4/1991 | Sharkawy . |
| 5,037,403 | 8/1991 | Garcia . |
| 5,046,503 | 9/1991 | Schneiderman . |
| 5,089,005 | 2/1992 | Harada . |
| 5,137,513 | 8/1992 | McInnes et al. . |
| 5,195,971 | 3/1993 | Sirhan . |
| 5,279,562 | 1/1994 | Sirhan et al. . |
| 5,334,154 | 8/1994 | Samson et al. . |
| 5,516,336 | 5/1996 | McInnes et al. . |
| 5,542,925 | 8/1996 | Orth . |
| 5,573,508 | 11/1996 | Thornton . |
| 5,573,509 | 11/1996 | Thornton . |
| 5,611,775 | 3/1997 | Machold et al. . |
| 5,766,203 | 6/1998 | Imran et al. .................... 606/198 |
| 5,776,140 | 7/1998 | Cottone .......................... 606/108 |
| 5,779,673 | 7/1998 | Roth et al. ...................... 604/101 |
| 5,830,181 | 11/1998 | Thornton . |
| 5,968,068 | 10/1999 | Dehdashtian et al. ............ 606/192 |

FOREIGN PATENT DOCUMENTS

| | | |
|---|---|---|
| 0 947 211 | 10/1999 | European Pat. Off. . |
| WO 96/39997 | 12/1996 | WIPO . |
| WO 98/10713 | 3/1998 | WIPO . |

*Primary Examiner*—Mark O. Polutta
*Assistant Examiner*—Michael J Hayes
*Attorney, Agent, or Firm*—Fulwider Patton Lee & Utecht, LLP

[57] ABSTRACT

A treatment catheter such as used for delivering a stent that includes a lumen for conducting contrast medium therethrough and shaped ports for vectoring contrast medium expelled therefrom toward the treatment site.

8 Claims, 2 Drawing Sheets

CONTRAST MEDIUM INJECTION DEVICE AND METHOD OF USE

BACKGROUND OF THE INVENTION

The present invention generally relates to the injection of contrast medium during vascular therapy and more particularly pertains to improved devices and methods for more efficiently and effectively delivering radiopaque dye to a treatment site.

During vascular therapy such as an angioplasty procedure or the stenting of a diseased area, it is highly desirable to be able to inject a contrast medium such as a radiopaque dye into the vessel upstream of the diseased site in order to check the flow past the site. This enables the physician to precisely locate the stenosis and assist in properly positioning the treatment device prior to treatment. After treatment, the injection of dye allows a determination to be made as to whether the procedure was successful or whether further treatment of the site, manipulation of the stent, or some other procedure is necessary.

A number of different techniques have previously been employed to deliver contrast medium to a treatment site. In one such method, contrast medium is injected via the guide or guiding catheter and more particularly through the annulus defined by the interior surface of the guide catheter and the exterior surface of the treating catheter extending therethrough. A number of shortcomings are, however, inherent in such approach. Because the guide catheter is relatively large and stiff, its access to smaller arteries and typically those being treated, is precluded. In the treatment of a coronary artery, for example, the guide catheter can be advanced no further than into the aortic root adjacent the mouth of the artery being treated. The treatment catheter must then extend therefrom into the treatment artery and on to the treatment site. As a consequence, in order to cause dye at a concentration sufficiently high to create a satisfactory image to be flushed past the treatment site, it is necessary to inject a relatively large quantity of the contrast medium. The quantity of dye must be sufficient to fill not only the entire volume of the treatment vessel proximal to the treatment site but must additionally compensate for the significant quantity that can be expected to leak into the aorta as no positive seal is formed between the distal end of the guide catheter and the entrance to the treatment vessel. Moreover, such quantity may have to be injected at multiple times or continuously for extended periods of time. Introduction of such large quantities may, however, be detrimental. Introduction of such large quantities may, however, be detrimental to tissue downstream of the injection site, in particular, brain tissue distal to a diseased carotid artery because it has the potential to displace oxygen carrying blood. Large contrast dye injections can also cause renal failure because the kidneys must process the additional fluid and restore the osmotic balance in the body. Delivery of the large quantity of dye that is needed for such a method is further complicated by the fact that the cross-sectional area of the annulus through which it is forced along the entire length of the catheter is rather small. As a result, injection under high pressure is needed to overcome the restricted flow.

An alternative to the use of the guide catheter to deliver contrast medium is the use of the guide wire lumen that is formed in the delivery catheter. After a standard over-the-wire design balloon catheter or stent deployment catheter is advanced to the treatment site, the guide wire can be removed and the catheter lumen used as a conduit for injection. This minimizes the amount of dye that is needed to generate an image of the treatment site and obviates the possibility of leakage into the aorta thus precluding the distribution of dye to other parts of the body. The principal disadvantage inherent in the use of such technique is that the guide wire must be removed. Because the guide wire must be replaced before another device can be inserted, in case of an emergency, such as a dislodged embolic particle, vessel spasm, or abrupt vessel closure, additional therapeutic devices cannot be placed quickly. For example, should plaque become dislodged by the injection, the stent would not yet be in position for expansion. Additionally, should such technique be used in conjunction with the delivery of a balloon expandable stent, the treatment catheter must be retracted for each viewing of the site. Each such shifting of the catheter within the artery increases the risk of dislodging plaque which upon being swept downstream and into the smaller arteries thereby embolizing and may even cause thrombosis. Moreover, attempting to precisely reposition the catheter in the treatment site after each injection may be difficult to achieve as well as time consuming.

A device and associated method is needed that minimizes the amount of dye that must be injected into the vasculature in order to provide a good visualization of the treatment site and obviates the need to shift any device within the artery in order to inject the dye.

SUMMARY OF THE INVENTION

The present invention overcomes the shortcomings of previously know contrast medium injection devices by providing a catheter configuration that enables contrast medium to be injected in an axial direction along the catheter's surface toward the diseased site being treated. Moreover, such injection is accomplished immediately upstream of the treatment site before, during, or after treatment and without the need to relocate or reposition the catheter in any way.

The device of the present invention consists of a lumen formed for conducting injection medium therethrough. Ports formed in the lumen that are positioned upstream and directly adjacent to treatment site set the lumen into fluid communication with the exterior surface of the catheter and vector the flow of contrast medium in the desired direction toward the treatment site. In an additional embodiment, the distal end of the lumen cooperates with a shaped stent holder to form a shaped distal vent for vectoring the flow of contrast fluid toward the lesion site. A further embodiment includes a lumen with ports placed proximally to the distal end of the lumen and stent holder cooperating with the distal end of the lumen to form a shaped distal vent, wherein the ports and the distal vent jointly vector fluid flow toward a lesion site.

The ported lumen may be incorporated in any number of catheter devices including but not limited to, stent delivery catheters and balloon dilatation catheters. In the case of stent delivery catheters, the invention may be adapted for use with both sheathed self-expanding stents as well as balloon expandable stents with or without sheaths.

Devices configured in accordance with the present invention initially enable contrast dye to be injected as the treatment site is approached in order to allow the precise location of the stenosis to be identified. Certain embodiments enable additional dye to be injected after positioning within the stenosed area but before treatment in order to allow the proper positioning of the treatment implement within the stenosed area to be verified. After treatment has been performed, dye is again injected in order to determine whether the desired results have been obtained.

These and other features and advantages of the present invention will become apparent from the following detailed description of the preferred embodiments which, taken in conjunction with the accompanying drawings, illustrate by way of example the principles of the invention.

DETAILED DESCRIPTION OF THE PREFERRED EMBODIMENTS

The present invention may be incorporated in any number of intravascular devices configured for specialized functions. The invention allows the injection of contrast medium to be accomplished without hindering the primary function of the intravascular device and without the need to retract or in any way shift the device. Visualization of the treatment site can thereby be quickly and easily realized without the risk of dislodging plaque, without the need to orient the device in any particular way and can be continued before, during and after advancing the device into position.

Figure 1:
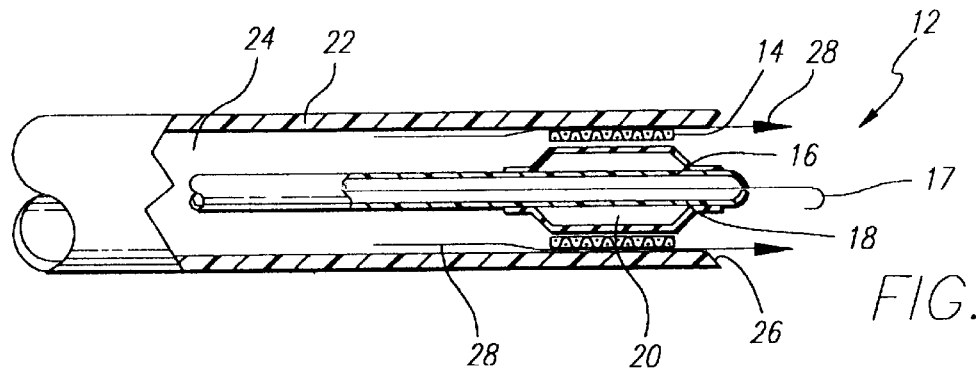
FIG. 1 is a cross-sectional view of a catheter of the present invention prior to deployment of the stent.

FIG. 1 illustrates a representative embodiment of the present invention. The invention is shown combined with and incorporated in delivery device 12 for self-expanding stent 14 prior to the stent's deployment. A conventionally configured guide wire catheter 16 defining guide wire lumen 18 is centrally disposed and has formed near its distal end a section of increased diameter which serves as stent holder 20. The guide wire 17 is shown extending from the lumen. Stent 14 is tightly collapsed about the holder and is confined to such configuration by restraining sheath 22 that is disposed thereabout. The restraining sheath in combination with the centrally disposed guide wire lumen define annular lumen 24. The interior surface 26 of the distal end of the restraining sheath has a flared profile. The interstitial space defined by the meshed or slotted structure of stent 14 is sufficiently open to allow contrast medium to be forced therethrough as represented by flow path arrows 28.

Figure 2:
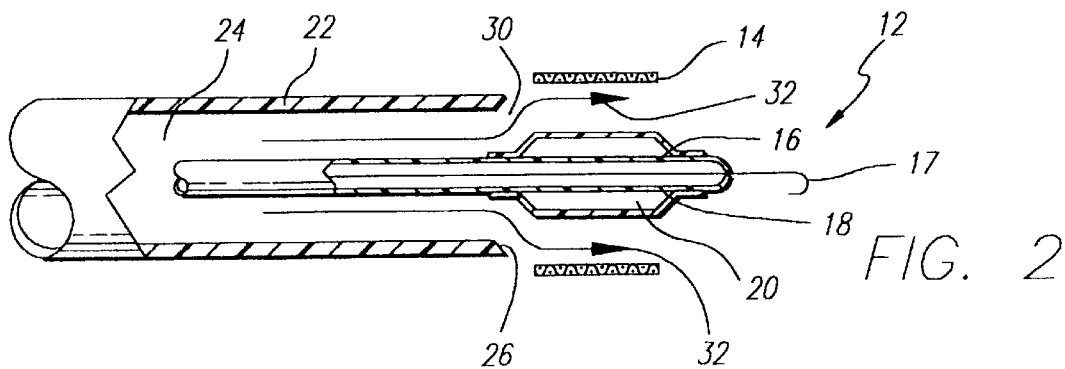
FIG. 2 is a cross-sectional view of the catheter of FIG. 1 after deployment of the stent.

FIG. 2 illustrates the device shown in FIG. 1 after deployment of the stent. Sheath 22 has been retracted such that the position of its distal end is just proximal of stent holder 20. As a consequence, stent 14 is shown in its deployed state with its enlarged diameter. The flared profile 26 of the distal end of restraining sheath or catheter 22 cooperates with the proximal end of stent holder 20 to define shaped vent 30 that vectors fluid expelled from annular lumen 24 toward the distal end of the device as represented by flow path arrows 32.

Figure 3:
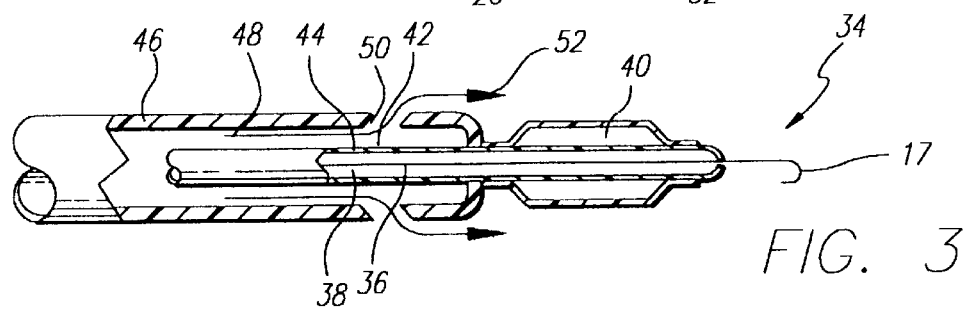
FIG. 3 is a cross-sectional view of an alternative embodiment catheter of the present invention.
Figure 4:
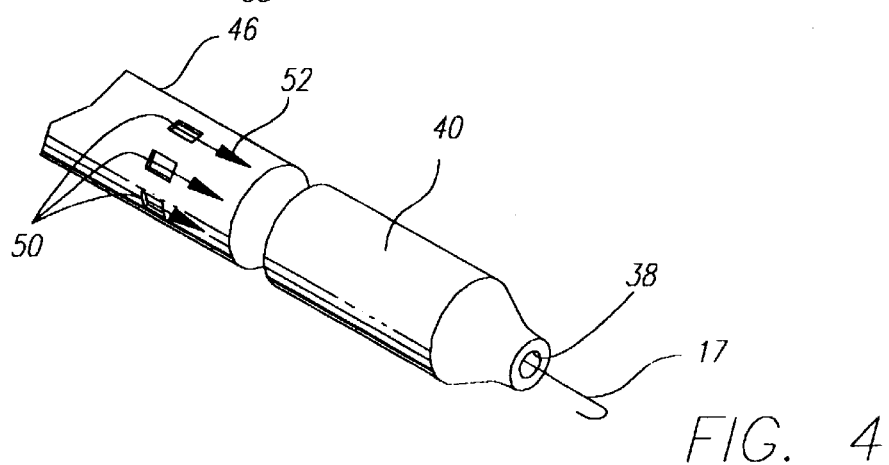
FIG. 4 is a perspective view of the catheter shown in FIG. 3.
Figure 5:
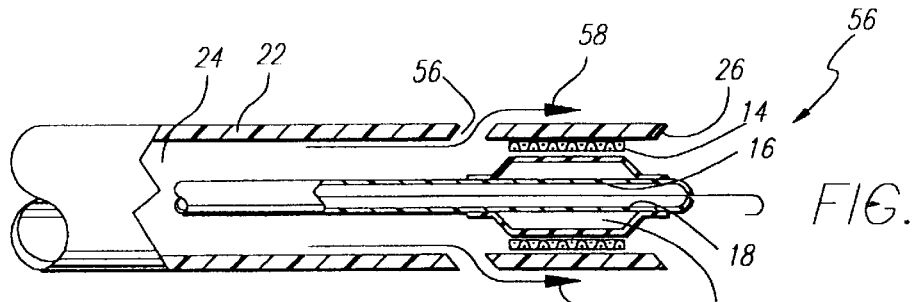
FIG. 5 is a cross-sectional view of another alternative embodiment of the present invention prior to deployment of the stent.
Figure 6:
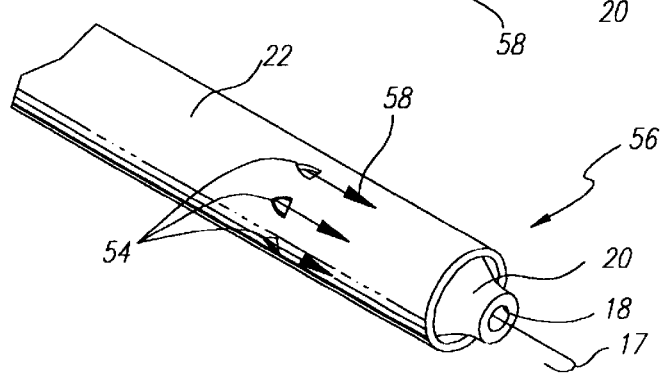
FIG. 6 is a perspective view of the device shown in FIG. 5.

FIGS. 3 and 4 illustrate another alternative embodiment 34 wherein a balloon catheter is modified in accordance with the present invention. The balloon catheter may be one sized and configured for pre-dilation, for delivery and expansion of a stent or for post dilation. In either adaption, central guide wire lumen 38 is defined by guide wire catheter 36 about which inflatable balloon 40 and inflation catheter 42 are disposed. Such balloon is inflated by fluid delivered via annular lumen 44 defined by the interior surface of inflation catheter 42 and the exterior surface of guide wire lumen 36. An additional catheter 46 is disposed about the exterior of balloon catheter to define another annular lumen 48. Exit ports 50 set such lumen into fluid communication with the exterior of the device. The ports are shaped so as to vector fluid in a distal direction as is represented by flow path arrows 52. The cross-sectional area of the ports is selected to be small enough to prevent premature leakage so that fluid is retained therein and air is excluded therefrom by capillary pressure. A check valve may be incorporated in the catheter as an alternative mechanism for preventing the premature leakage of fluid from the lumen and the incursion of air thereinto. While FIG. 3 shows the device in cross-section, the perspective view of FIG. 4 more clearly shows the placement and distribution of multiple exit ports 50. One or more exit ports may be formed in the catheter in accordance with the present invention.

Figure 7:
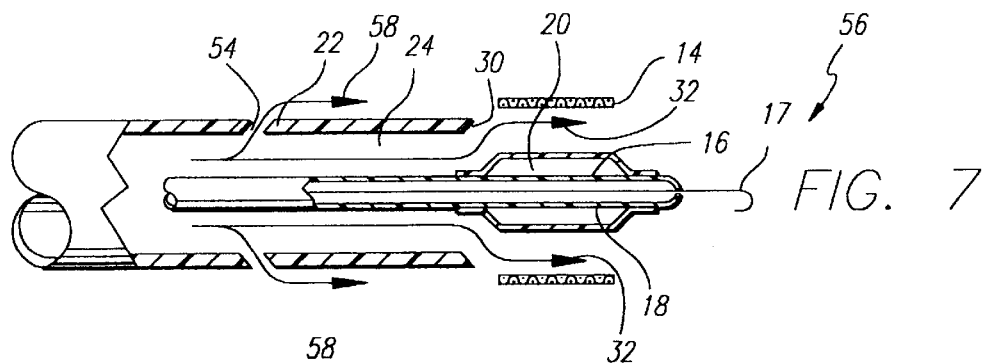
FIG. 7 is a cross-sectional view of the embodiment shown in FIG. 5 after deployment of the stent.
Figure 8:
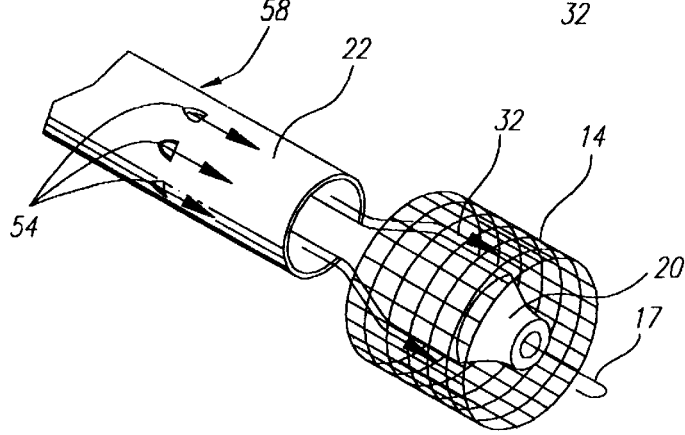
FIG. 8 is a perspective view of the device shown in FIG. 7.

FIGS. 5–8, illustrate another alternative embodiment of the present invention wherein shaped ports 54 are added to the embodiment shown in FIGS. 1 and 2. The perspective views of device 56 in FIGS. 6 and 8 clearly show the circumferential distribution of multiple ports. The cross-sectional area of ports 54 is selected to be greater than the cross-sectional area of flow path 28 through stent 14. Consequently, fluid forced through lumen 24 prior to deployment of the stent will be expelled through ports 54 as is shown by flow paths 58. After deployment, as shown in FIGS. 7 and 8, the cross-sectional area of flow path 32 past the distal end of the sheath is greater than the cross-sectional area of the flow path through ports 54 and as a result, substantially greater flow will issue from distal vent 30 than from shaped port 54.

The catheters are constructed and assembled by conventional methods. The ports may be formed by molding an attachment that is subsequently affixed to the catheter either by welding or by the use of an adhesive. Alternatively, the shaped ports are cut directly into the catheter with a computer-controlled laser.

In use, such as in the stenting of a coronary artery with the device illustrated in FIGS. 5–8, a guide catheter is first introduced into the aorta by, for example, a femoral or brachial artery. The guide catheter is advanced into position adjacent the treatment artery within the aortic root as is known in the art. Once in place, the guide catheter acts as a conduit to allow the stent-carrying delivery catheter 56 and guide wire 17 to be advanced into place. After guide wire 17 is inside the treatment artery, it can be advanced through and past the stenosis. The treatment catheter 56 is then advanced over the guide wire toward the stenosis. By pressurizing the proximal end of pre-filled lumen 24, radiopaque dye is forced through ports 54 and carried along by the bloodflow past the stenosed area to allow the site to be accurately visualized. Dye is continually or intermittently injected as catheter 56 is further advanced to allow visualization of stent 14 as it is positioned within the stenosis. Once the physician is satisfied with the positioning of stent 14, sheath 22 is retracted to release stent 14 thereby allowing it to expand against the walls of the artery. Further injection of radiopaque dye, predominately via distal vent 30 and to a lesser extent via shaped port 54, allows the now stented area to be visualized to in turn allow a determination to be made as to the success of the procedure.

While a particular form of the invention has been illustrated and described, it will also be apparent to those skilled in the art that various modifications can be made without departing from the spirit and scope of the invention. Accordingly, it is not intended that the invention be limited except by the appended claims.

What is claimed is:

1. A stent delivery device comprising:
   a sheath-catheter for delivery of a contrast medium, the sheath-catheter including a distal end and ports located proximally from the sheath-catheter's distal end;
   a stent delivery catheter slidably received in the sheath-catheter, the stent delivery catheter having a shaped stent holder;
   a distal vent, wherein the distal end of the sheath-catheter and the shaped stent holder cooperate to form the distal vent when the stent delivery catheter is deployed from the sheath-catheter;
   the ports and the distal vent functioning to direct contrast medium towards a lesion, wherein the contrast medium flows from the ports when the delivery catheter is retracted within the sheath-catheter, and the contrast medium flows through both the ports and the distal vent with substantially more fluid flowing through the vent when the stent delivery catheter is deployed.

2. The stent delivery device of claim 1, wherein the ports in the sheath-catheter are circumferentially distributed about the catheter.

3. The stent delivery device of claim 1, wherein the ports in the sheath-catheter are shaped to vector contrast fluid in a distal direction.

4. The stent delivery device of claim 1, wherein the stent delivery catheter further includes a stent carried thereon and positioned distally of the ports in the sheath-catheter.

5. The stent delivery device of claim 4, wherein the cross-sectional area of the ports is selected to be greater than the interstitial flow area of the stent.

6. The stent delivery device of claim 1, wherein the ports have a cross-sectional area selected to be sufficiently small such that capillary pressure prevents the contrast medium from prematurely leaking from the sheath-catheter.

7. A method for visualizing a vascular treatment site, comprising:
   providing a stent delivery device that includes a sheath-catheter for delivery of a contrast medium, the sheath-catheter having a distal end and ports located proximally from the sheath-catheter's distal end, the stent delivery device further including a stent delivery catheter slidably received in the sheath-catheter, the stent delivery catheter having a shaped stent holder, wherein the distal end of the sheath-catheter and the shaped stent holder cooperate to form a distal vent when the stent delivery catheter is deployed from the sheath-catheter;
   advancing the stent delivery device towards the treatment site so as to position a stent carried by the stent delivery device within the treatment site;
   forcing contrast medium through the sheath-catheter wherein the contrast medium flows through the ports downstream to the treatment site enabling the treatment site to be visualized during positioning of the stent; and
   deploying the stent within the treatment site wherein contrast fluid is released through the distal vent allowing for visualization of the stented treatment site.

8. The method of claim 7, further comprising retracting the sheath catheter and forcing the contrast medium out through the ports.

* * * * *